United States Patent [19]

Childers et al.

[11] Patent Number: 5,015,480

[45] Date of Patent: May 14, 1991

[54] FILM COATING FORMULATIONS

[75] Inventors: Ray F. Childers, Carmel; Peter L. Oren, Nobelsville; Werner M. K. Seidler, Indianapolis, all of Ind.

[73] Assignee: Eli Lilly and Company, Indianapolis, Ind.

[21] Appl. No.: 125,087

[22] Filed: Nov. 25, 1987

[51] Int. Cl.$^5$ .............................................. A61K 9/14
[52] U.S. Cl. .................................. 424/486; 424/465; 424/470; 424/493; 424/495; 424/497; 524/53
[58] Field of Search ............... 424/486, 470, 465, 486, 424/470, 465, 493, 497, 495; 524/53

[56] References Cited

U.S. PATENT DOCUMENTS

| | | | |
|---|---|---|---|
| 4,462,982 | 7/1984 | Samejimal et al. | 424/495 |
| 4,650,666 | 3/1987 | Izutsu et al. | 424/493 |
| 4,695,467 | 9/1987 | Uemura et al. | 424/465 |
| 4,708,874 | 11/1987 | De Haan et al. | 424/470 |

OTHER PUBLICATIONS

*Remington's Pharmaceutical Sciences*, 17th Edition, 1985, Chapter 91, p. 1634.
K. Lehmann, *Acta. Pharm. Fenn.* 91, 225–238 (1982).
*Pullulan:Production and Applications.*
*Pullulan, Features and Applications.*

Primary Examiner—Thurman K. Page
Assistant Examiner—P. L. Prater
Attorney, Agent, or Firm—Joseph A. Jones; Leroy Whitaker

[57] ABSTRACT

Aqueous diffusion coating formulations suitable for use on pharmaceutical dosage forms comprising an admixture of an insoluble polymer component of a copolymer of ethylacrylate and methylmethacrylate and as a hydrophilic component the polysaccharide pullulan. When applied to the substrate of choice, said formulations provide coatings exhibiting good mechanical strength and flexibility.

34 Claims, No Drawings

FILM COATING FORMULATIONS

Solid pharmaceutical dosage forms, most notably tablets, have been coated with a wide variety of materials utilizing various processes for years. The reasons for this include the aesthetic as well as the practical. For example, tablet coatings can mask an unpleasant taste or odor, can increase ease of ingestion by the patient and can serve to improve the ultimate appearance of the dosage form. Similarly, coatings can protect the product from the effects of air, moisture and light, can improve product identification and can facilitate handling in packaging and filling lines during manufacture.

Typically, pharmaceutical dosage forms may be sugar coated or film coated. Sugar coating is a multi-step and tedious process. In the hands of a skilled worker sugar coated products are elegant in appearance, however, certain problems beset the process and the ultimate product. For example, the sugar coating process requires that the tablets be kept constantly tumbling thus presenting difficulties such as fragmenting of those units not strong enough to withstand the stress encountered during the process. Also, color nonuniformity, rough or overly soft coatings or marbling may present additional problems to be addressed.

In order to overcome some of these difficulties, film coating was introduced to the pharmaceutical industry in the 1950's with certain advantages inherent in the process. Film coating involves the deposition of a thin, uniform, typically polymeric membrane to the substrate usually by a spray technique. Certain of the advantages include minimal weight increase of the ultimate dosage form, reduction in processing times, improved resistance to chipping, and the like. However, notwithstanding these advantages certain difficulties are attendant with the film coating process including the tendency to laminate if the tablets being coated are not of sufficient strength, the inability to hide defects in the tablet core, mottling and the like. Ironically, the use of organic solvents in film coating, one of the major reasons for the process advantages, also presents some of the major disadvantages. Plainly, due to their volatility, the use of organic solvents in the film coating process can lead to flammability hazards as well as concerns over environmental effects and potential toxicity to the operators. Additionally, organic solvents add to the cost of the overall process either due to the costs of the solvents per se or costs encountered in reducing any potential hazards thereof.

Film coatings have also been utilized to modify the release of the constituents of the core tablet as, for example, via enteric coating wherein the polymer employed in the coating is essentially impervious to gastric pH while being soluble in the increased pH of the intestines. A further application of film coating lies in the formulation of extended release coatings which help eliminate the need for multiple dose regimens of a particular therapeutic agent. Various types of extended release approaches are known. One such is referred to as a diffusion coating which involves the deposit of a coating (usually from an organic solvent) on a soluble substrate core with a porous, water-permeable but insoluble membrane. The release profile of the therapeutic agent can be modified by the inclusion of water soluble substances within the membrane. These substances are dissolved by the gastrointestinal fluids thereby creating pores within the film. These pores allow the gastrointestinal fluids to pass through the membrane and dissolve the therapeutic agent within the tablet core. The diffusion rate can be controlled by the thickness and composition of the diffusion membrane. For this system to function properly, the constituents of the diffusion coating formulation must exhibit good mechanical strength and flexibility. Unfortunately, however, it is a frequently encountered problem that such coating formulations, when deposited on the substrate, lack the requisite mechanical strength and flexibility thereby leading to rupture of the deposited film during dissolution in the gastrointestinal tract. This in turn permits the sudden release of the entire contents of the substrate containing the therapeutic agent in a phenomenon referred to as "dose dumping". Such a situation is clearly undesirable for extended release dosage forms given the higher amount of therapeutic agent found therein as compared to conventional formulations.

The present invention obviates this problem by providing an aqueous diffusion coating which exhibits good mechanical strength and flexibility when applied to a substrate thereby reducing the possibility of membrane rupture and inadvertent release of the constituents. Additionally, by varying the relative concentrations of the components of the coating formulation of the present invention, the release rate of the therapeutic agent present in the substrate may be modified so as to fit any desired profile. Further, the coating formulation of the present invention utilizes an aqueous solvent system thereby eliminating the disadvantages of organic solvents in the film coating process delineated above.

SUMMARY OF THE INVENTION

The present invention provides an aqueous diffusion coating formulation for a pharmaceutical dosage form comprising an admixture of: (a) an insoluble polymer component of a copolymer of ethylacrylate and methylmethacrylate; and (b) as a hydrophilic component the polysaccharide pullulan. Also disclosed and claimed are discrete, solid pharmaceutical dosage forms covered with said aqueous diffusion coating formulation.

DETAILED DESCRIPTION OF THE INVENTION

The insoluble polymer component of the aqueous diffusion coating formulation is a copolymer of ethylacrylate and methylmethacrylate, preferably in a 2:1 monomer ratio, respectively. Such a copolymer is readily prepared by known methodologies such as described by Lehmann et al. in *Pharm. Ind.* 34, 894–899 (1972) which is incorporated herein by reference. Acrylic resins such as this for use as pharmaceutical coatings are also commercially available. A particularly preferred copolymer of ethylacrylate and methylmethacrylate is one known commercially as EUDRAGIT E 30 D which is available from Rohm Pharma, Darmstadt, West Germany. EUDRAGIT E 30 D is provided as an aqueous dispersion (30 percent by weight solids) of said copolymer of ethylacrylate and methylmethacrylate in a 2:1 monomer ratio, respectively and has a molecular weight of 800,000. Further information pertaining to EUDRAGIT E 30 D may be found in *Acta. Pharm. Fenn.*, 91, 225–238 (1982) and references cited therein, which is incorporated herein by reference.

The hydrophilic component of the aqueous diffusion coating formulation is the polysaccharide pullulan. Pullulan is an edible, water-soluble, viscous polysaccharide which is extracellularly elaborated by *Aureobasidium*

*pullulans,* formerly designated as *Pullularia pullulans,* also commonly known as "black yeast". Pullulan is an alpha-glucan with a linear structure of maltotriose units (i.e., units of three alpha-1,4-linked glucose molecules) repeatedly polymerized via alpha-1,6 linkages on the terminal glucose residues. Pullulan is commercially available from Hayashibara Biochemical Laboratories, Inc., Okayama, Japan. Further information regarding the production of pullulan may be obtained from the following publications, each of which is incorporated herein by reference: Wallenfels et al., *Angew Chem.* 73, 245 (1961); Wallenfels et al., *Biochem. Z.* 341, 433 (1965); and Ueda et al., *Appl. Microbiol.* 11, 211 (1963).

As an alternative to pullulan as the hydrophilic component, a modified food starch known commercially as Amaizo ARD 2326 may be used. Technically, Amaizo ARD 2326 is a pregelatinized, modified waxy maize starch which has a low dextrose equivalent and high molecular weight, is soluble in water, possesses low viscosity and has a bland flavor. Amaizo ARD 2326 is commercially available from American Maize-Products Company, Hammond, Ind., U.S.A.

The insoluble polymer component may be added to water and used as an aqueous dispersion containing from 30 to 90 percent by weight of the total solids present in said aqueous diffusion coating formulation. Preferably, this amount will be 60 percent by weight of total solids present. With respect to the hydrophilic component, said component will be present in the aqueous coating formulation in an amount of from 10 to 60 percent by weight of the total solids present in said formulation. Preferably, this amount is 35 percent by weight of total solids present. The total amount of solids by weight representing the insoluble polymer component and the hydrophilic component of the aqueous diffusion coating formulation will be 65 to 100 percent. Further, the weight percent of total solids from the aqueous coating formulation relative to the weight of the substrate to which it is applied may range from 5 to 20 percent by weight and is preferably 10 percent by weight. The skilled artisan will readily recognize that amounts of either component of the present aqueous diffusion coating formulation outside of the ranges presented above may still provide a coating with the requisite mechanical strength and flexibility so as to be operable as a diffusion coating as contemplated herein. Any such aqueous coating formulations are deemed to be within the scope and spirit of the present invention. Similarly, it will be readily apparent to the skilled artisan that acrylic resins other than the ethylacrylate-methylmethacrylate copolymer disclosed herein will find utility as the insoluble polymer component of the aqueous diffusion coating formulations of the present invention. For example, other suitable polymers include aqueous dispersions of copolymers synthesized from acrylic acid and methacrylic acid esters having a low content of quaternary ammonium groups. Two such copolymers are commercially available from Rohm Pharma, Darmstadt, West Germany under the tradenames EUDRAGIT RL and EUDRAGIT RS.

The skilled artisan will further appreciate that certain adjuvants may be included in the aqueous coating formulations which are well-recognized in the art. These include, but are not limited to, adjuvants such as permeability enhancers, plasticizers, antitacking agents and the like. For example, conventional permeability enhancers include polyethylene glycol, polyvinylpyrrolidone, sucrose, lactose and other like sugars. When present in the aqueous diffusion coating formulation of the instant invention, a permeability enhancer will be present in a range of from 5 to 60 percent by weight of total solids present in the aqueous diffusion coating formulation, preferably 30 percent by weight of total solids present. Examples of conventional plasticizers include glycerin, propylene glycol, polyethylene glycols, acetylated monoglycerides, citrate esters (such as triethyl citrate), triacetin and various phthalate esters such as diethyl phthalate. When present in the aqueous diffusion coating formulation of the instant invention, one or more such plasticizers will be present in a range of from 0 to 15 percent, preferably 2.5 percent by weight of total solids present. Similarly, conventional anti-tacking agents include talc, magnesium stearate, calcium stearate, stearic acid, and the like. When present in the aqueous diffusion coating formulations of the instant invention such anti-tacking agents will be present in a range of from 1 to 10 percent, preferably 5 percent by weight of total solids present. When present in the aqueous diffusion coating formulations of the instant invention a preferred anti-tacking agent is talc. Other such adjuvants which are conventional in the art and which will be apparent to the skilled artisan may be incorporated into the aqueous diffusion coating formulations of the present invention. Again, the skilled artisan will recognize that the ranges set forth above for these adjuvants are merely exemplary for what is conventional. The presence thereof in the aqueous coating formulations in amounts which happen to fall outside of these ranges are deemed to be within the spirit and scope of the invention, where a coating may still be provided with the requisite mechanical strength and flexibility so as to be operable as a diffusion coating as contemplated herein.

The aqueous diffusion coating formulations of the present invention may be readily prepared by methodologies well known in the art. Typically, to the desired amount of hydrophilic component is added, with continuous mixing, any of the desired adjuvants such as described previously (i.e., permeability enhancers, plasticizers, anti-tacking agents, colorants and the like). Separately, an aqueous dispersion of the insoluble polymer (i.e., the ethylacrylate-methylmethacrylate copolymer) is prepared having the desired amount of the polymer contained therein. Alternatively, as noted above, the dispersion may be purchased from commercial sources having the desired amount of polymer present. Said aqueous dispersion is then added to the hydrophilic polysaccharide component (including any added adjuvants) and the resultant aqueous coating formulation is then continually mixed throughout the substrate coating operation as described below. Further general information relating to methods for preparing formulations such as described herein invention may be obtained from *Acta. Pharm. Fenn.*, supra.

The aqueous diffusion coating formulation of the present invention is applied to the substrate of choice using conventional methodologies. For example, the aqueous diffusion coating formulations may be sprayed on the substrate in a rotating coating pan. The spray means may be of the hydraulic nature where the coating liquid is pumped under pressure to a spray nozzle where atomization of the liquid occurs. Alternatively, the coating formulation may be applied via an air-spray where the liquid is atomized by compressed air at the aperture of the spray nozzle. Spray techniques allow the delivery of the finely atomized aqueous diffusion coating formulation to contact the substrate while in continuous motion. The coating pans may be conventional such as those used in sugar coating processes or may be of the type more specifically designed for film coating including Pelligrini pans, Strunck apparatus, immersed sword apparatus, Wurster fluidized bed apparatus, and the like. All such equipment have means for providing heated air for drying as well as exhaust means for removal of the solvent. Further information pertinent to film coating processes and equipment may be obtained from *Remington's Pharmaceutical Sciences*, 17th Edition, Mack Publishing Company, Easton, Pa. (1985) which is incorporated herein by reference.

The pharmaceutical dosage form is a substrate to which the aqueous coating formulation of the present invention is applied and may be any such substrate containing a therapeutic agent which is known in the art. Such substrates include tablets and capsules of any size, pellets, granules, marumes, nonpareils, spheres and the like. Tablets are a preferred substrate. The skilled artisan will readily appreciate that the substrate formulation should be such as to avoid the inclusion of ingredients which would place any unnecessary stress on the ultimate film coating. While the present aqueous diffusion coating formulation provides films of good mechanical strength and flexibility, additives to the substrate which promote rapid disintegration such as starches, methylcellulose, agar, bentonite and the like should be avoided. Conversely, additives which are soluble in the gastrointestinal fluids and hence promote diffusion of the therapeutic constituent of the substrate are preferably employed. Such additives include sugars such as sucrose, lactose or mannose and organic acids such as ascorbic, citric and fumaric acid.

The substrates themselves are prepared by well-known means which are conventional in the art. For example, compressed tablet substrates may contain, in addition to the therapeutic agent, various excipients such as diluents, binders, lubricants, glidants and the like. The tablet substrate may be prepared by wet or dry-granulation methods or by direct compression and produced by any of a wide variety of tabletting machines. Any other such substrates are prepared by conventional techniques such as disclosed in *Remington's Pharmaceutical Sciences*, supra or other such treatises available to the skilled artisan.

As alluded to earlier, by varying the ratio of the insoluble polymer component to the hydrophilic component of the aqueous diffusion coating formulation the release rate of the therapeutic agent from the substrate may be varied over a wide range. Further, by changing the composition of the hydrophilic component by the addition of one or more of the adjuvants described above (in an otherwise fixed insoluble-soluble component ratio) the release rate of the therapeutic agent can also be influenced. In all such instances, the film retains its good mechanical strength and flexibility which will not rupture during dissolution. This aspect of the present invention will become apparent in light of the following examples which are provided as a means of illustrating the invention and are not to be construed as a limitation thereon.

EXAMPLE 1

An aqueous diffusion coating formulation (20 percent by weight total solids) containing 60 percent by weight of total solids present EUDRAGIT E 30 D (as the source of the ethylacrylate-methylmethacrylate copolymer), 35 percent by weight of total solids present pullulan and 5 percent by weight of total solids present talc was prepared as follows. Seventy grams (g) of pullulan was dissolved in about 400 g of purified water with a propeller type mixer at low speed. Talc (10 g) was wetted and suspended with a minor amount of purified water and was then added to the above aqueous mixture of pullulan. To the resultant admixture was added 400 g of EUDRAGIT E 30 D and sufficient purified water to make the weight of the final mixture 1000 g. The aqueous diffusion coating formulation was continuously stirred throughout the substrate coating operation described in Example 2.

Using the above procedures, the aqueous diffusion coating formulations shown in Table I were prepared (wherein all values shown represent percent by weight of total solids present). In Table I, the insoluble component in each formulation was EUDRAGIT E 30 D brand of ethylacrylate-methylmethacrylate copolymer obtained from Rohm Pharma, supra. Additionally, each of the formulations shown in Table I contained, as an anti-tacking agent, 5 percent by weight talc (except formulation number 123 which contained 7.5 percent by weight talc).

TABLE I

| Formulation No. | Insoluble Component | Hydrophilic Component | |
|---|---|---|---|
| | | Pullulan | Amaizo ARD 2326 |
| 97 | 65 | 12$^{a,b}$ | — |
| 99 | 55 | 25$^{c,d}$ | — |
| 114 | 60 | 20$^{c,d}$ | — |
| 118 | 60 | 30$^{d,e}$ | — |
| 121 | 60 | 32.5$^d$ | — |
| 123 | 60 | 32.5 | — |
| 125 | 60 | 35 | — |
| 172 | 65 | 13.5$^{d,f}$ | — |
| 186 | 50 | — | 42.5$^d$ |
| 196 | 40 | 52.5$^d$ | — |
| 197 | 85 | 10 | — |

$^a$13 percent by weight polyvinylpryyolidone added to the hydrophilic component
$^b$5 percent by weight polyethylene glycol 3350 added to the hydrophilic component
$^c$12.5 percent by weight polyvinylpyrrolidone added to the hydrophilic component
$^d$2.5 percent by weight polyethylene glycol 3350 added to the hydrophilic component
$^e$2.5 percent by weight polyvinylpyrrolidone added to the hydrophilic component
$^f$14 percent by weight polyvinylpyrrolidone added to the hydrophilic component

EXAMPLE 2

Potassium chloride tablet cores were prepared as follows. Twenty kilograms (kg) of potassium chloride (crystalline powder) was poured through a number 14 mesh screen after which 19.5 kg was placed into a V-blender and 0.5 kg was hand-mixed with 10 g mineral oil. The hand-mixed portion was then added to the quantity in the V-blender and the entire contents was mixed for 10 minutes. This mixture was then compressed into tablets by a Colton 204 Rotary Compression Machine with 0.5 inch deep concave punches to a hardness of 14–16 kg, a thickness of 0.225–0.240 inch and a tablet weight of 1.0 g.

To each one of five batches of these tablet cores was applied one of the following aqueous diffusion coating formulations as shown in Table I: 196, 99, 114, 97 and 186. The coating formulation was applied as follows.

Generally, 1.5 kg quantities of the potassium chloride tablet cores were placed into a conventional 14 inch coating pan with hot air applied to the tablet bed rotating at about 30 revolutions per minute. Seven hundred fifty grams of the desired aqueous diffusion coating was applied to the tablet cores using a DeVilbis spray gun operating at 35-40 pounds of air pressure at an initial rate of 4 grams per minute for the first hour and then increasing to 5 grams per minute until completion. During the operation, the reservoir for the aqueous diffusion coating formulation (20 percent by weight of total solids) was intermittently agitated by hand. The theoretical amount of coating solids applied to the tablet cores was 10 percent (weight/weight).

The dissolution rates for sample tablets from each batch were determined by the method prescribed by the United States Pharmacopeia XXI, 1985 (referred to hereafter as USP XXI) for potassium chloride extended release tablets. USP XXI is incorporated herein by reference. Briefly, dissolution apparatus 2 of USP XXI was used with purified water as the dissolution media. ACS reagent grade potassium chloride was used as the reference standard. The dissolution samples to be assayed were collected for analysis at the desired times from 900 milliliters (ml) of purified water heated to 37° centigrade at a stirring speed of 50 revolutions per minute. The reference standards and samples to be assayed were analyzed by atomic absorption spectroscopy, a selective chloride probe or other suitable method and the values received for the reference standards were recorded. From this information, the concentration of the samples to be assayed was determined. As a control, the 1 g KCl diffusion membrane coated tablet KALIPOR (AB Ferrosan, Sweden) was used. The coating formulation for KALIPOR is a polyvinyl chloride/vinyl acetate containing micronized sucrose deposited from an organic solvent system. See, *J. Pharm. Sci.* 72(7)772-775 (1983). The results of this dissolution study are set forth in Table II, and are expressed as the cumulative percent potassium chloride released from the tablets with the coating formulation shown at the time indicated.

TABLE II

Dissolution of 1 gram Potassium Chloride Tablets

| Hours | Formulation No. | | | | | Control |
|---|---|---|---|---|---|---|
| | 196 | 99 | 114 | 97 | 186 | |
| 1 | 41 | 18 | 11 | 2 | 14 | 10 |
| 2 | 74 | 38 | 27 | 6 | 27 | 26 |
| 3 | 93 | 56 | 40 | 11 | 42 | 41 |
| 4 | 99 | 70 | 50 | 18 | 55 | 55 |
| 5 | | 83 | 63 | 20 | 67 | 65 |
| 6 | | 92 | 74 | 23 | 78 | 79 |
| 7 | | 98 | 82 | 27 | 87 | 85 |
| 8 | | | 93 | 31 | 94 | 96 |
| Total | 100 | 100 | 100 | 102 | 102 | 100 |

As can be seen from the data in Table II, by varying the ratio of insoluble polymer to the hydrophilic component, the dissolution rate for the tablet constituents can be adjusted over a wide range. In all cases, a flexible, mechanically strong coating that did not rupture during dissolution was obtained.

EXAMPLE 3

Following essentially the same procedures described in Example 2, 1 g sodium chloride tablet cores were covered with aqueous diffusion coating formulation number 121. Three separate batches were prepared with a 5 percent, 7.5 percent or 10 percent coating of the formulation applied, respectively. The results of the dissolution study are set forth in Table III where the values expressed refer to the cumulative percent sodium chloride dissolved at the hour shown.

TABLE III

Dissolution of 1 Gram NaCl Tablets[a]

| Hours | Coating | | |
|---|---|---|---|
| | 5% | 7.5% | 10% |
| 1 | 25 | 16 | 9 |
| 2 | 43 | 35 | 19 |
| 3 | 60 | 53 | 32 |
| 4 | 81 | 65 | 47 |
| 5 | 103 | 74 | 58 |
| 6 | | 91 | 67 |
| 7 | | 100 | 82 |
| 8 | | | 95 |
| Total | 103 | 100 | 95 |

[a]Coated with formulation number 121

EXAMPLE 4

The procedure of Example 3 was repeated using aqueous diffusion coating formulation number 118. The results of the dissolution study are shown in Table IV where the values expressed refer to the cumulative percent sodium chloride dissolved at the hour shown.

TABLE IV

Dissolution of 1 Gram NaCl Tablets[a]

| Hours | Coating | | |
|---|---|---|---|
| | 5% | 7.5% | 10% |
| 1 | 25 | 14 | 6 |
| 2 | 37 | 27 | 16 |
| 3 | 59 | 40 | 26 |
| 4 | 74 | 50 | 34 |
| 5 | 80 | 63 | 41 |
| 6 | 87 | 74 | 47 |
| 7 | 96 | 81 | 54 |
| 8 | 97 | 89 | 59 |
| 9 | | 97 | 64 |
| 10 | | | 71 |
| 11 | | | 81 |
| 12 | | | 89 |
| Total | 97 | 97 | 89 |

[a]Coated with formulation number 118

EXAMPLE 5

Following procedures essentially as described in Example 2, 0.5 g tablet cores of the antibiotic cephalexin as the hydrochloride salt were coated with aqueous diffusion coating formulation number 121 to yield a 12.5 percent coating by weight. The results of the dissolution study (using the USP XXI dissolution apparatus 1, a 10 mesh basket at 100 revolutions per minute) are shown in Table V where the values expressed refer to the cumulative percent cephalexin dissolved at the hour shown.

TABLE V

Dissolution of 0.5 Gram Cephalexin Tablets

| Hour | 12.5% Coating |
|---|---|
| 1 | 13 |
| 2 | 27 |
| 3 | 37 |
| 4 | 45 |
| 5 | 54 |
| 6 | 62 |
| 7 | 69 |
| 8 | 76 |

These data show that the aqueous diffusion coating formulation used provided a relatively constant release of the antibiotic over an 8 hour period. By contrast, the tablet cores per se and the tablet cores plus a sealant were tested for dissolution rate in the same system. Both exhibited 100 percent dissolution within 1 hour.

EXAMPLE 6

Following procedures essentially as described in Example 2, two separate batches of 300 milligram (mg) imipramine hydrochloride tablet cores were film coated with aqueous diffusion coating formulation number 172 to both 7.5 and 12.5 percent coating by weight, respectively. The results of the dissolution study (conducted in 1000 ml of purified water in USP XXI dissolution apparatus 2 at 100 revolutions per minute) are shown in Table VI where the values expressed refer to the cumulative percent imipramine hydrochloride dissolved at the hour shown.

TABLE VI

Dissolution of 300 mg Imipramine HCl Tablets

| Hours | Coating 7.5% | Coating 12.5% |
|---|---|---|
| 1 | 11 | 3 |
| 2 | 38 | 14 |
| 3 | 61 | 30 |
| 4 | 79 | 46 |
| 5 | 84 | 58 |
| 6 |  | 67 |
| 7 |  | 79 |

EXAMPLE 7

In order to show that the drug release rate can be influenced by changing the compositions of the hydrophilic component (by varying the adjuvants), formulation numbers 114, 118, 121, 123 and 125 were applied to five separate batches of 1 g KCl tablets as described in Example 2. For each of these formulations (except for formulation 123), the ratio of the total insoluble polymer component to hydrophilic component (including insoluble and soluble adjuvants) remained constant at 65:35 percent by weight, respectively. For formulation 123, the ratio was 67.5:32.5 percent by weight. These data are set forth in Table VII where the values expressed refer to the cumulative percent KCl dissolved at the hour shown. As described in Example 2, KALIPOR was again used as a control.

TABLE VII

Effect of Composition Components on Dissolution of 1 Gram KCl Tablets

| Hours | 114 | 118 | 121 | 123 | 125 | Control |
|---|---|---|---|---|---|---|
| 1 | 11 | 10 | 9 | 4 | 4 | 10 |
| 2 | 27 | 22 | 21 | 12 | 7 | 26 |
| 3 | 40 | 35 | 32 | 21 | 14 | 41 |
| 4 | 50 | 44 | 49 | 28 | 18 | 55 |
| 5 | 63 | 55 | 61 | 37 | 23 | 65 |
| 6 | 74 | 65 | 73 | 44 | 28 | 79 |
| 7 | 82 | 76 | 85 | 52 | 34 | 85 |
| 8 | 93 | 86 | 99 | 60 | 39 | 96 |
| 9 | — | 92 | 101 | 66 | 44 | — |
| Total | 100 | 100 | 101 | — | — | 100 |

EXAMPLE 8

In order to demonstrate that the aqueous diffusion coating formulations are versatile over a broad range of substrates, the release of 50 mg of the antihypertensive agent Pinacidil from 400–500 core pellets approximately 1 millimeter in diameter was controlled by the application of coating formulation 197. Three separate batches of the core pellets were prepared with 10 percent, 15 percent or 17.5 percent coating of the formulation applied, respectively. The results of this dissolution study (conducted in 900 ml of 0.1 normal HCl in USP XXI dissolution apparatus 1 at 100 revolutions per minute) are set forth in Table VIII where the values expressed refer to the cumulative percent of Pinacidil dissolved at the hour shown.

TABLE VIII

Dissolution Study of Pinacidil

| Hours | Coating 10% | Coating 15% | Coating 17.5% |
|---|---|---|---|
| 0.5 | 28 | 7 | 8 |
| 1 | 66 | 20 | 12 |
| 2 | 91 | 62 | 46 |
| 3 | 96 | 85 | 76 |
| 4 |  | 95 | 88 |
| 5 |  | 100 | 94 |
| 6 |  |  | 97 |

As expected, because of the higher specific surface area of this dosage form relative to a single unit tablet, an increased amount of a less permeable coating than, for example, formulations 97 or 99 was required to achieve comparable drug release profiles. The data presented in Table VIII clearly show the extent of control of release which may be achieved with the present aqueous diffusion coating formulations on relatively high specific surface area substrates.

We claim:

1. An aqueous diffusion coating formulation for a pharmaceutical dosage form comprising an admixture of: (a) an aqueous dispersion of an insoluble polymer component of a copolymer of 2 parts of ethylacrylate and one part methylmethacrylate; and (b) as a hydrophilic component the polysaccharide pullulan; wherein (1) the insoluble polymer component is present in an amount of from 30 to 90 percent by weight of the total solids present in said coating formulation and the hydrophilic component is present in an amount of from 10 to 60 percent by weight of total solids present in said coating formulation and (2) the total amount of solids by weight representing the insoluble polymer component and the hydrophilic component of the coating formulation is from 65 to 100 percent of said coating formulation.

2. The aqueous diffusion coating formulation of claim 1 wherein said insoluble polymer component is present in an amount of 60 percent by weight of total solids present in said coating formulation and said hydrophilic component is present in an amount of 35 percent by weight of total solids present in said coating formulation.

3. The aqueous diffusion coating formulation of claim 1 containing adjuvants selected from the group consisting of permeability enhancers, plasticizers and anti-tacking agents.

4. The aqueous diffusion coating formulation of claim 2 containing adjuvants selected from the group consisting of permeability enhancers, plasticizers and anti-tacking agents.

5. The aqueous diffusion coating formulation of claim 3 wherein the anti-tacking agent is talc and is present in said aqueous diffusion coating formulation in an amount of from 1 to 10 percent by weight of total solids present in said formulation.

6. The aqueous diffusion coating formulation of claim 4 wherein the anti-tacking agent is talc and is present in said aqueous diffusion coating formulation in an amount of from 1 to 10 percent by weight of total solids present in said formulation.

7. The aqueous diffusion coating formulation of claim 5 wherein the talc is present in an amount of 5 percent by weight of total solids present in said coating formulation.

8. The aqueous diffusion coating formulation of claim 6 wherein the talc is present in an amount of 5 percent by weight of total solids present in said coating formulation.

9. An aqueous diffusion coating formulation of claim 1 for a pharmaceutical dosage form comprising an admixture of from 30 to 90 percent by weight of total solids supplied as a copolymer of ethylacrylate and methylmethacrylate in a 2:1 monomer ratio, said copolymer having an average molecular weight of 800,000, and from 10 to 60 percent by weight of total solids supplied as pullulan.

10. The aqueous diffusion coating formulation of claim 9 wherein said admixture is 60 percent by weight of total solids supplied as a copolymer of ethylacrylate and methylmethacrylate and 35 percent by weight of total solids present as pullulan.

11. The aqueous diffusion coating formulation claim 9 containing adjuvants selected from the group consisting of permeability enhancers, plasticizers and anti-tacking agents.

12. The aqueous diffusion coating formulation of claim 10 containing adjuvants selected from the group consisting of permeability enhancers, plasticizers and anti-tacking agents.

13. The aqueous diffusion coating formulation of claim 11 wherein the anti-tacking agent is talc and is present in an amount of from 1 to 10 percent by weight of total solids present in said formulation.

14. The aqueous diffusion coating formulation of claim 12 wherein the anti-tacking agent is talc and is present in an amount of from 1 to 10 percent by weight of total solids present in said formulation.

15. The aqueous diffusion coating formulation of claim 13 wherein the talc is present in an amount of 5 percent by weight of total solids present in said formulation.

16. The aqueous diffusion coating formulation of claim 14 wherein the talc is present in an amount of 5 percent by weight of total solids present in said formulation.

17. A discrete solid pharmaceutical dosage form selected from the group consisting of tablets, capsules, pellets, granules, marumes, nonpareils and spheres said dosage form coated with an aqueous diffusion coating formulation comprising an admixture of: (a) an aqueous dispersion of an insoluble polymer component of a copolymer of ethylacrylate and methylmethacrylate; and (b) as a hydrophilic component the polysaccharide pullulan.

18. The dosage form of claim 17 wherein the insoluble polymer component of said aqueous diffusion coating formulation is a copolymer of ethylacrylate and methylmethacrylate in a monomer ratio of 2:1, respectively.

19. The dosage form of claim 18 wherein the insoluble polymer component of said aqueous diffusion coating formulation is present in an amount of from 30 to 90 percent by weight of total solids present in said formulation and the hydrophilic component of said aqueous diffusion coating formulation is present in an amount of from 10 to 60 percent by weight of total solids present in said formulation.

20. The dosage form of claim 19 wherein the insoluble polymer component of said aqueous diffusion coating formulation is present in an amount of 60 percent by weight of total solids present in said formulation and the hydrophilic component of said aqueous diffusion coating formulation is present in an amount of 35 percent by weight of total solids present in said formulation.

21. The dosage form of claim 19 wherein the aqueous diffusion coating formulation contains adjuvants selected from the group consisting of permeability enhancers, plasticizers and anti-tacking agents.

22. The dosage form of claim 20 wherein the aqueous diffusion coating formulation contains adjuvants selected from the group consisting of permeability enhancers, plasticizers and anti-tacking agents.

23. The dosage form of claim 21 wherein the aqueous diffusion coating formulation con talc as the anti-tacking agent and is present in an amount of from 1 to 10 percent by weight of total solids present in said aqueous diffusion coating formulation.

24. The dosage form of claim 22 wherein the aqueous diffusion coating formulation talc as the anti-tacking agent and is present in an amount of from 1 to 10 percent by weight of total solids present in said aqueous diffusion coating formulation.

25. The dosage form of claim 23 wherein the aqueous diffusion coating formulation contains talc in an amount of 5 percent by weight of total solids present in said formulation.

26. The dosage form of claim 24 wherein the aqueous diffusion coating formulation contains talc in an amount of 5 percent by weight of total solids present in said coating formulation.

27. A discrete solid pharmaceutical dosage form selected from the group consisting of tablets, capsules, pellets, granules, marumes, nonpareils and spheres said dosage form coated with an aqueous diffusion coating formulation of claim 1 comprising an admixture of from 30 to 90 percent by weight of total solids supplied as a copolymer of ethylacrylate and methylmethacrylate in a 2:1 monomer ratio, said copolymer having an average molecular weight of 800,000, and from 10 to 60 percent by weight of total solids supplied as pullulan.

28. The dosage form of claim 27 wherein the aqueous diffusion coating formulation is an admixture of 60 percent by weight of total solids supplied as a copolymer of ethylacrylate and methylmethacrylate and 35 percent by weight pullulan.

29. The dosage form of claim 27 wherein the aqueous diffusion coating formulation contains adjuvants selected from the group consisting of permeability enhancers, plasticizers and anti-tacking agents.

30. The dosage form of claim 28 wherein the aqueous diffusion coating formulation contains adjuvants selected from the group consisting of permeability enhancers, plasticizers and anti-tacking agents.

31. The dosage form of claim 29 wherein the aqueous diffusion coating formulation contains talc as an anti-tacking agent in an amount of from 1 to 10 percent by weight of total solids present in said formulation.

32. The dosage form of claim 30 wherein the aqueous diffusion coating formulation contains talc as an anti-tacking agent in an amount of from 1 to 10 percent by weight of total solids present in said formulation.

33. The dosage form of claim 31 wherein the aqueous diffusion coating formulation contains talc as an anti-tacking agent in an amount of 5 percent by weight of total solids present in said formulation.

34. The dosage form of claim 32 wherein the aqueous diffusion coating formulation contains talc as an anti-tacking agent in an amount of 5 percent by weight of total solids present in said formulation.

* * * * *